(12) United States Patent
Hou et al.

(10) Patent No.: US 7,922,648 B1
(45) Date of Patent: Apr. 12, 2011

(54) MYOCARDIAL INFARCTION PATCH FOR MINIMALLY INVASIVE IMPLANT

(75) Inventors: Wenbo Hou, Lancaster, CA (US); Sheldon Williams, Green Valley, CA (US)

(73) Assignee: Pacesetter, Inc., Sylmar, CA (US)

( * ) Notice: Subject to any disclaimer, the term of this patent is extended or adjusted under 35 U.S.C. 154(b) by 1115 days.

(21) Appl. No.: 11/354,698

(22) Filed: Feb. 14, 2006

(51) Int. Cl.
*A61F 2/00* (2006.01)
*A61F 2/02* (2006.01)

(52) U.S. Cl. .......................................... 600/37; 600/16

(58) Field of Classification Search .................. 600/29, 600/30, 37, 16–18; 607/129; 623/11.11, 623/23.72, 23.76; 601/151, 153
See application file for complete search history.

(56) References Cited

U.S. PATENT DOCUMENTS

| | | | | |
|---|---|---|---|---|
| 4,030,509 A | * | 6/1977 | Heilman et al. | 607/17 |
| 4,827,932 A | * | 5/1989 | Ideker et al. | 607/2 |
| 5,042,463 A | * | 8/1991 | Lekholm | 607/129 |
| 5,122,155 A | * | 6/1992 | Eberbach | 606/213 |
| 5,324,328 A | * | 6/1994 | Li et al. | 607/129 |
| 5,330,524 A | * | 7/1994 | Mar | 607/129 |
| 5,336,254 A | * | 8/1994 | Brennen et al. | 607/129 |
| 5,366,460 A | * | 11/1994 | Eberbach | 606/151 |
| 5,391,200 A | * | 2/1995 | KenKnight et al. | 607/129 |
| 5,702,343 A | * | 12/1997 | Alferness | 600/37 |
| 6,293,906 B1 | * | 9/2001 | Vanden Hoek et al. | 600/37 |
| 6,659,950 B2 | | 12/2003 | Taheri | 600/439 |
| 6,695,769 B2 | | 2/2004 | French et al. | 600/37 |
| 7,060,023 B2 | * | 6/2006 | French et al. | 600/37 |
| 7,270,669 B1 | * | 9/2007 | Sra | 606/129 |
| 2001/0018549 A1 | * | 8/2001 | Scetbon | 600/30 |
| 2002/0151868 A1 | | 10/2002 | Taheri | 604/507 |
| 2004/0208845 A1 | | 10/2004 | Michal et al. | 424/78.24 |
| 2005/0187620 A1 | | 8/2005 | Pai et al. | 623/2.37 |

FOREIGN PATENT DOCUMENTS

WO WO 2004/019592 A2 10/2004

* cited by examiner

*Primary Examiner* — Charles A Marmor, II
*Assistant Examiner* — Catherine E. Burk

(57) ABSTRACT

A fixation section and a rim form a myocardial patch for implant in the pericardial space. The fixation section is adapted to promote fibrosis to secure the patch in place. The rim is secured to and surrounds at least a portion of the fixation section and has a lumen. The patch is adapted to transition between a collapsed state and an expanded state. A stylet is passed through the lumen to force the patch into a collapsed state and is removed when the patch is positioned to allow the patch to expand and engage the epicardial surface.

19 Claims, 4 Drawing Sheets

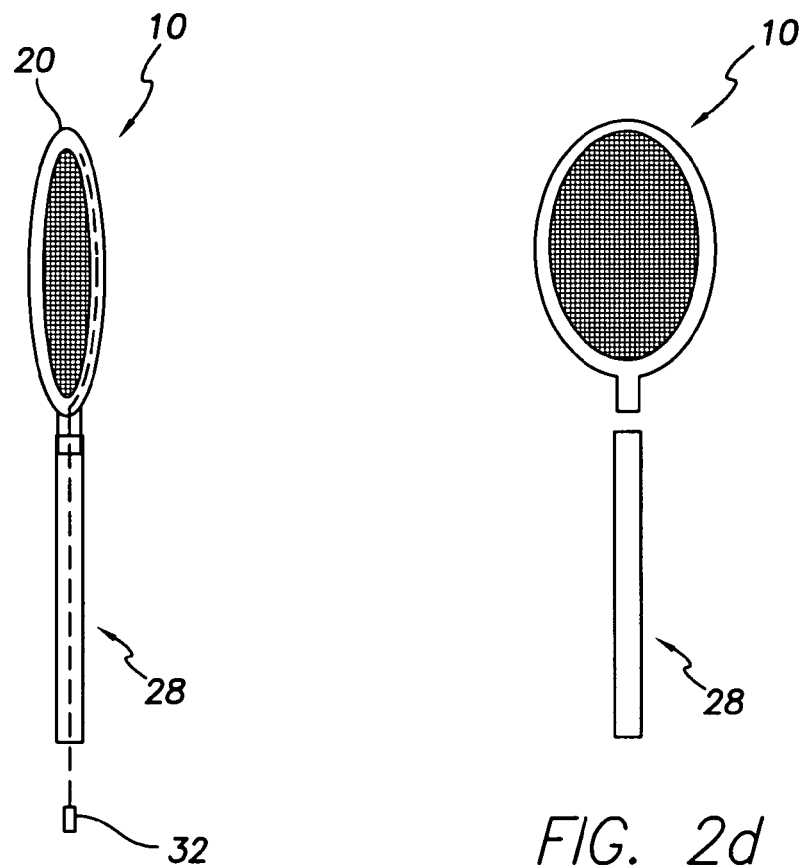
FIG. 2c
FIG. 2d
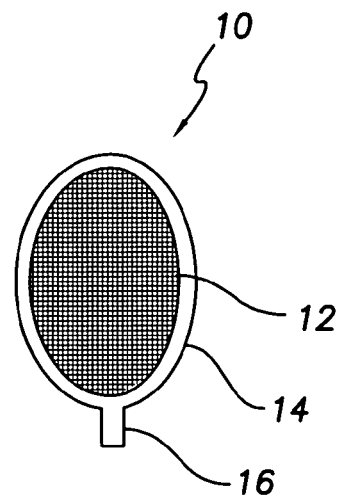
FIG. 2e

MYOCARDIAL INFARCTION PATCH FOR MINIMALLY INVASIVE IMPLANT

FIELD OF THE INVENTION

The invention relates generally to devices for the treatment of myocardial infarction and more particularly to a myocardial patch for implant using minimally invasive techniques.

BACKGROUND

A myocardial infarction (MI) occurs when a coronary artery becomes occluded and can no longer supply blood to the myocardial tissue. When a myocardial infarction occurs, the myocardial tissue that is no longer receiving adequate blood flow dies and is replaced with scar tissue. Within seconds of a myocardial infarction, the under-perfused myocardial cells no longer contract, leading to abnormal wall motion, high wall stresses within and surrounding the infarct, and depressed ventricular function. Infarct expansion and ventricular remodeling are caused by these high stresses at the junction between the infarcted tissue and the normal myocardium. These high stresses eventually kill or severely depress function in the still viable myocardial cells. This results in a wave of dysfunctional tissue spreading out from the original myocardial infarct region.

Known treatments for MI include invasive, open-chest surgical approaches to exclude, isolate, or remove the infarct region. Other potential surgical approaches, that also require the chest to be opened, include the application of heat to shrink the infarcted, scarred tissue, followed by the suturing of a patch onto the infarcted region. Other open-chest surgical treatments envision surrounding the heart, or a significant portion thereof, with a jacket to prevent further remodeling of the heart.

SUMMARY

Briefly, and in general terms, the invention relates to myocardial patches and methods of implanting such patches using minimally invasive techniques, such as a subxyphoid approach. In one aspect of the invention, a fixation section and a rim form a myocardial patch. Both the fixation section and the patch are adapted to transition between a collapsed state and an expanded state. The fixation section is adapted to promote fibrosis to secure the patch in place. The rim is secured to and surrounds at least a portion of the fixation section and has a lumen. The lumen functions to receive a stylet that forces the patch to collapse for implant. The lumen may also function to receive adhesive for securing the patch to the myocardium.

In another aspect, the invention relates to a method of implanting a myocardial patch on an epicardial surface of a patient. The patch includes a fixation structure at least partially surrounded by a rim defining a lumen. The patch is implanted by positioning the distal end of a lumen structure in the pericardial space; inserting a stylet into the rim lumen of the patch to at least partially collapse the patch; pushing the patch through the lumen structure and into the pericardial space; and removing the stylet to allow the patch to assume its expanded state.

BRIEF DESCRIPTION OF THE DRAWINGS

FIGS. 2a-2e are schematic representations of the various mechanical stage of the patch of FIG. 1a during a delivery process;

DETAILED DESCRIPTION

The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designations will be used to refer to like parts or elements throughout.

Figure 1A:
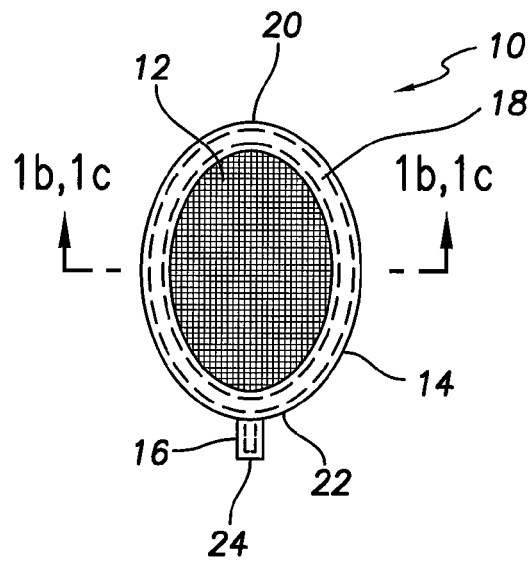
FIG. 1a is a plan view of a myocardial patch configured in accordance with the invention.
Figure 1B:
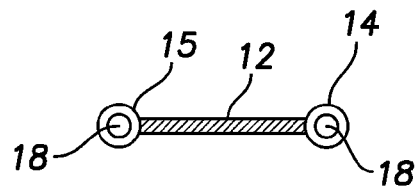
FIG. 1b is a cross section of one configuration of the patch of FIG. 1a taken along line 1b-1b.
Figure 1C:
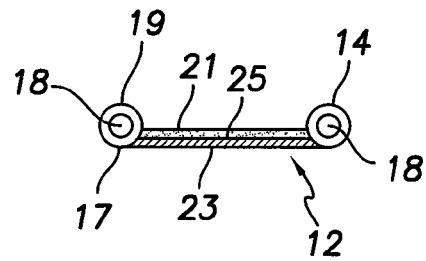
FIG. 1c is a cross section of another configuration of the patch of FIG. 1a taken along line 1c-1c.

Referring now to the drawings and particularly to FIGS. 1a-1c, there is shown a myocardial patch 10 configured in accordance with the invention. The patch 10 includes a fixation section 12, a rim 14 and a connection junction 16. The rim 14 defines a lumen 18, which in one configuration extends completely around the rim. In other configurations, the rim lumen 18 may only extend partially around the rim, for example, between the connection junction 16 and the distal region 20 of the rim.

The connection junction 16 is joined to the rim 14 at the proximal region 22 of the rim and includes a lumen 24 that communicates with the rim lumen 18. The connection junction 16 may be a separate part that is secured to the rim 14 using bonding, gluing or other chemical or mechanical means. Alternatively, the connection junction 16 may be formed as an integral part of the rim 14. In the embodiment of FIG. 1a, the rim 14 completely surrounds the fixation section 12. In other configurations of the patch 10, the rim 14 may only partially surround the fixation section 12, for example by extending one-half or three-quarters of the way around the fixation section 12.

The fixation section 12 is formed to have sufficient flexibility to allow for the section to assume a collapsed state upon the application of force. In one embodiment, the fixation section 12 may be made of a polyester polymer with an open weave mesh, such as a Dacron mesh. The fixation section 12 may also be formed to exhibit elastic properties, for example, by the inclusion of an elastomeric material. For example, the fixation section 12 may be formed of polyester polymer woven together with an elastic metal to form a mesh. The elasticity of the fixation section allows the fixation section to resume its expanded state upon the removal of a collapsing force.

The fixation section has a large enough surface area to induce a sufficient degree of tissue over growth to provide stable, chronic fixation of the patch 10 to the myocardium. The thickness of the fixation section 12 and variations of its structure may also be used to achieve desired fixation results. For example in the case of a mesh section, the weave structure may be made looser or tighter to achieve different results. Generally, the stability of the patch 10 increases with increasing surface area of the fixation section 12. Therefore, the surface area of the fixation section 12 may be varied in accordance with the size of the MI site and doctor preference.

With reference to FIGS. 1b and 1c, the patch may have a bidirectional configuration (FIG. 1b) or a unidirectional configuration (FIG. 1c). In the bidirectional configuration, the rim 14 and the fixation section 12 are secured together such that the fixation section lies within the inner perimeter 15 of the rim. In this configuration, the patch 10 may be implanted with either side of the fixation section 12 adjacent the epicardial surface of the heart.

In the unidirectional configuration, as shown in FIG. 1c, the rim 14 may be described as having an epicardial side 17 and a pericardial-sac side 19. Likewise, the fixation section 12 may be described as having an epicardial side 23 and a pericardial-sac side 25. The fixation section 12 is secured to epicardial side of the rim 14. In this configuration, the patch 10 is implanted so the epicardial sides 17, 23 of the rim 14 and fixation section 12 are adjacent the epicardial surface of the heart. To ensure proper placement of the patch 10, the fixation section 12 may include a fluoroscopic marker, such as the letter S, on its epicardial side 23. Under fluoroscopy, improper orientation of the patch 10 is detected if the letter S appears backwards.

A layer of anti-fibrosis material 21, such as silicone, may be applied to the pericardial-sac side 25 of the fixation section 25 to prevent fibrosis attachment between the pericardial sac and the patch 10. Anti-fibrosis material may also be applied to other areas of the patch 10, such as the pericardial-sac side 19 of the rim 14.

In either patch configuration, the rim 14 and fixation section 12 are secured together using bonding, gluing, suturing or any other chemical or mechanical means. The rim 14 may be configured as a coil, formed of a biocompatible metal having elastic properties, such as MP35N. A coiled rim 14 may also be formed of Nitinol. In this configuration the inside of the coil defines the rim lumen 18. Alternatively, the rim 14 may be configured as a tube, formed of a biocompatible polymer, such as silicone, polyurethane or PEEK, ePTFE etc. In another configuration, the rim may include both tube and coil aspects, such as alternating segments of tube and coil. The rim 14 may also be molded onto the fixation section 12.

The rim 14, like the fixation section 12, is formed to have sufficient flexibility to allow the rim to assume a collapsed state upon the application of force. The rim 14 is further formed to exhibit elastic properties that allow the rim to resume its expanded state upon the removal of a collapsing force. Through its attachment to the fixation section 12, the rim 14—with its elastic property—functions to force the fixation section to return to its expanded state regardless of whether the fixation section itself is elastic.

Figure 2A:
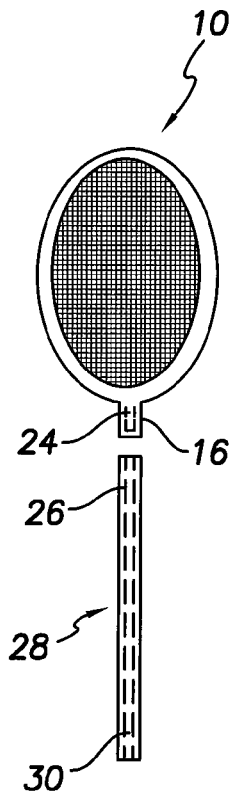
Figure 2B:
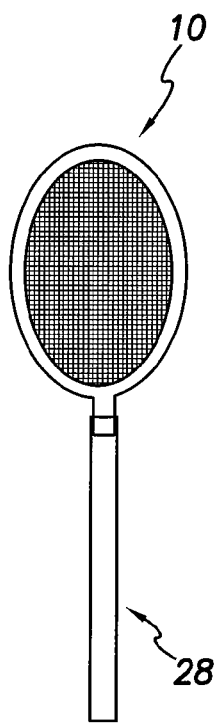

Referring to FIGS. 2a-2e, the various mechanical stages of a patch delivery process are shown. In FIG. 2a, the connection junction 16 of a patch 10 engages the distal end 26 of an elongated body 28 and is held securely in place, as shown in FIG. 2b. The elongated body 28 is adapted to slide through an introducer and includes a lumen 30 for feeding a stylet into the connection junction 16 of the patch 10. The elongated body 28 includes a coil structure along its length and an insulating sheath made of biocompatible material such as silicone or polyurethane, similar to that included in cardiac leads. The coil allows for torque transmission between the proximal and distal ends of the body.

The connection between the elongated body 28 and the connection junction 16 is provided by mechanical means such as a friction fit or a threaded junction. In the case of a friction fit, the respective inner and outer diameters of the elongated body 28 and the connection junction 16 are sized to fit tightly together. In the case of a threaded junction, the elongated body 28 and the connection junction 16 include mating screw threads.

Next, as shown in FIG. 2c, a stylet 32 is inserted through the series of lumens 30, 24, 18 to the distal region 20 of the rim 14. The stylet forces the rim 14 to assume a collapsed state, which in turn forces the fixation section 12 to collapse. The collapsed patch 10 is then implanted into the pericardium sac through an introducer using an implantation technique, such as a subxiphoid technique, which is described later below with reference to FIG. 3. If the patch is too thick to be collapsed, it can be rolled up and pushed through the introducer. The rim 14 is typically more rigid than the fixation section 12 and thus provides increased mechanical stability to the fixation section. Also, as described further below, during patch 10 implant the elasticity of the rim promotes full expansion of the fixation section 12, which ensures sufficient coupling of the section to the heart surface.

Continuing with FIGS. 2a-2e, upon implantation of the patch 10 at the desired location on the epicardial surface, the stylet 32 is removed and the rim 14 and fixation section 12 assume their expanded states, as shown in FIG. 2b. If necessary, the location of the patch 10 is manipulated using the elongated body 28. After final location of the patch 10, the elongated body 28 is disconnected from the rim 14 as shown in FIG. 2d. In the case of a friction fit between the elongated body 28 and the connection junction 18, the body is disconnected by pulling on the elongated body. In the case of a threaded junction, the body 28 is disconnected by rotating the body until it disengages the threads of the connection junction 18. The elongated body 28 is then removed from the patient, leaving only the patch 10, as shown in FIG. 2e.

Figure 3:
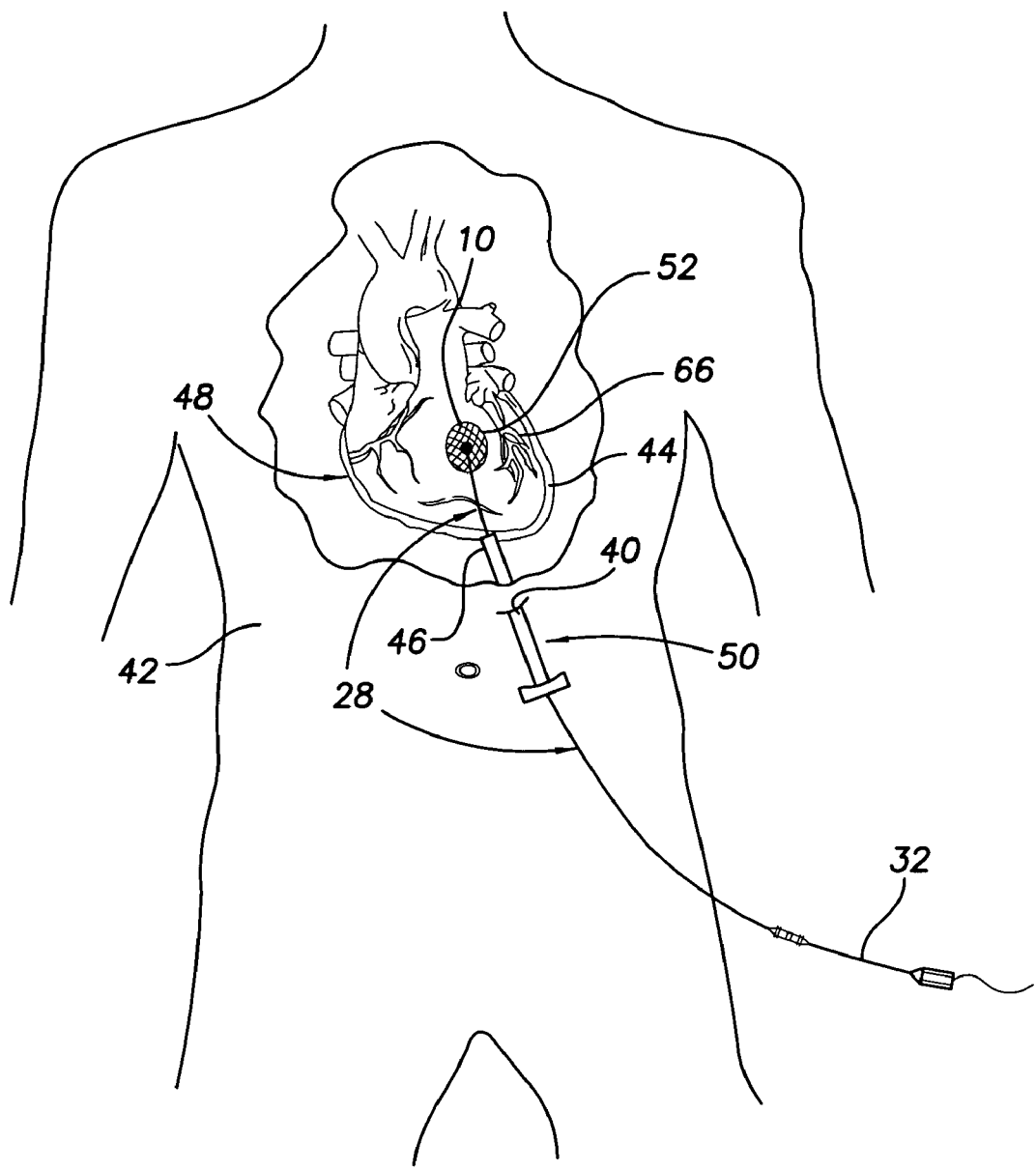
FIG. 3 is a schematic illustration of a myocardial patch coupled with a patient's heart.

Referring to FIG. 3 in a patch implantation technique, one or more intercostal or subxyphoid incisions 40 for receiving various instruments are made in the mid-chest region 42 of a patient. Although FIG. 3 illustrates one incision, it will be evident that two or more incisions may also be employed. In addition, the precise locations and sizes of the incisions and the instruments used may vary depending upon the patient's anatomy and the surgeon's preferences. Each incision may accommodate a trocar (not shown) for facilitating the insertion and manipulation of one of the instruments.

According to one approach, a puncture needle (not shown) having a center lumen is inserted into the mid-chest region 42 via a subxiphoid or intercostal approach and introduced into the pericardial space 44 through a puncture 46 in the pericardial sac 48. The needle is guided through the pericardial space using fluoroscopic or X-ray imaging and small amounts of contrast media. Alternatively, endoscopy or ultrasound can also be used for visualization during the implant procedure. Once successful entry into the pericardial space is documented, a guidewire is inserted into the needle and advanced into the pericardial space.

A dilator (not shown) and an introducer 50 are then advanced over the guidewire and into the pericardial space 44 to expand the passageway through the puncture site 46. Once inside the pericardial space 44 the dilator and guidewire may be removed. The patch 10 is then positioned in the pericardial space 44 at a desired location through the introducer 50 using a stylet 32 as previously described with reference to FIGS. 2a-2e. The desirable location is over a MI site 52, which may be determined prior to or during patch implant using well known techniques in the art, such as echo-graphic imaging.

Figure 4:
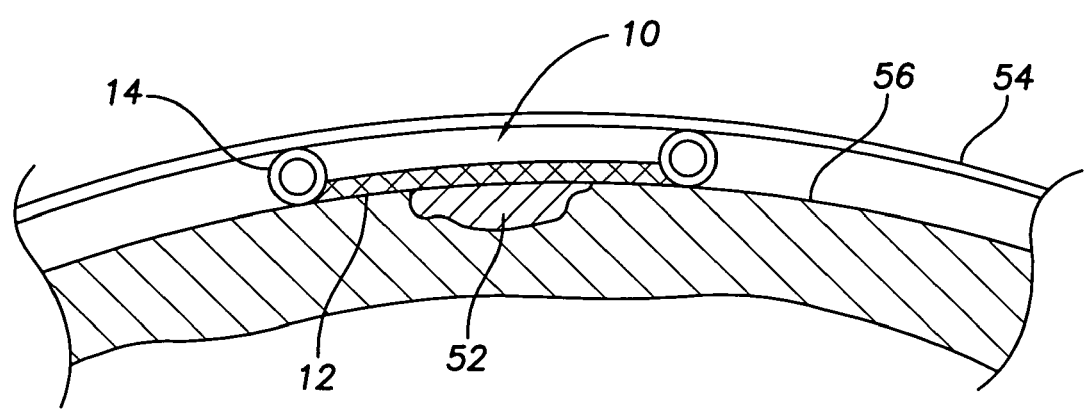
FIG. 4 is a cross section of an implanted patch.

With reference to FIG. 4, during placement of a unidirectional patch 10 over the MI site 52, the pericardium 54 pushes down on the rim 14 to promote good contact between the fixation section 12 and the epicardial surface 56 at the MI site and thereby provides acute fixation of the patch. Additional acute fixation of the patch 10 may be provided by applying adhesive between the patch and the epicardial surface 56. The adhesive may be a light-activated acrylic or cyanoacrylate adhesive such as those offered by Loctite Corporation, Rocky Hill, Conn. Versions of such Loctite® acrylic adhesives and Loctite® FlashCure™ cyanoacrylate adhesives can be cured upon exposure to UV light or Cyanoacrylate surgical adhesive such as Eastman 910, or Indermil® tissue Adhesive by syneture or the biocompatible glues like Coseal® and Tisseel® by Baxter, or Bioglue by CryoLife. In case to use UV adhesive, another access to intrapericardial space may be needed for delivering the UV light to the adhesive. The adhesive may be applied by injection through the lumen 30 (FIG. 2a) of the elongated body 28. In the case of a coil rim 14, the adhesive seeps through the space between coils, thereby gluing the patch 10 to the epicardium. In the case of the tube rim 14, holes (not shown) may be provided in the rim to allow for the glue to pass through. Alternatively, the adhesive may be delivered between the patch 10 and the epicardial surface through a separate delivery device inserted in the pericardial space or through a common delivery device including a first port for delivering the patch 10 and a second port for injecting the adhesive.

In an alternative delivery technique an elongated body is not used. Instead, a stylet 30 is inserted through the connection junction 16 up to the distal end 20 of the patch 10 to collapse the rim 14 and fixation section 12. The patch 10 and stylet 30 are then inserted into the introducer 50 and the stylet is used to push the patch 10 through the introducer into the pericardial space.

It will be apparent from the foregoing that while particular forms of the invention have been illustrated and described, various modifications can be made without departing from the spirit and scope of the invention. For example, while the patch shown and described is elliptical shaped, other patch shapes are possible, such as circles. Consequently, the specific structural and functional details disclosed herein are merely representative and do not limit the scope of the invention. The scope of the invention should be ascertained with reference to the claims.

What is claimed is:

1. A method of implanting a myocardial patch on an epicardial surface of a patient, the patch having a fixation structure at least partially surrounded by a rim defining a lumen along the length of the rim, said method comprising:
   positioning the distal end of a lumen structure in the pericardial space;
   inserting a stylet into and along the length of the rim lumen of the patch, wherein the application of force by the stylet along the length of the rim lumen causes the patch to at least partially collapse;
   pushing the patch through the lumen structure and into the pericardial space; and
   removing the stylet from along the length of the rim lumen, wherein the absence of the application of force by the stylet along the length of the rim lumen allows the patch to assume its expanded state.

2. The method of claim 1 wherein positioning the lumen structure comprises accessing the pericardial space using a minimally invasive technique.

3. The method of claim 2 wherein the minimally invasive technique is the subxiphoid approach.

4. The method of claim 1 further comprising applying an adhesive material between the epicardial surface and the patch.

5. The method of claim 1 further comprising attaching the patch to an elongated body having a lumen and wherein the stylet is inserted into the rim lumen through the elongated-body lumen and the patch is pushed through the lumen structure in the pericardial space using the elongated body.

6. The method of claim 5 further comprising disconnecting the elongated body from the patch.

7. The method of claim 5 wherein the rim includes openings and further comprising injecting an adhesive material through the elongated-body lumen into the rim lumen and through the openings.

8. A myocardial patch system comprising:
   a stylet;
   a myocardial patch including a fixation section adapted to promote fibrosis and a rim structure secured to and surrounding at least a portion of the fixation section and having a lumen there through extending along the length of the rim and configured to receive the stylet, wherein the patch is adapted to assume a collapsed state due to the application of force by the stylet when the stylet extends along the length of the rim lumen and to assume an expanded state due to the absence of the application of force by the stylet when the stylet does not extend along the length of the rim lumen; and
   an elongated body having a lumen there through and adapted for connection and disconnection from the rim structure, such that the rim lumen and the body lumen are in communication with each other when connected.

9. The system of claim 8 wherein the elongated body connects to the rim structure through a friction fit.

10. The system of claim 8 wherein the elongated body connects to the rim structure through mating screw threads.

11. The system of claim 8 wherein the rim comprises a coil defining the rim lumen.

12. The system of claim 11 wherein the coil is formed of a biocompatible metal.

13. The system of claim 8 wherein the rim comprises a tube defining a lumen.

14. The system of claim 13 wherein the tube is formed of a biocompatible polymer.

15. The system of claim 13 wherein the tube comprises a plurality of holes.

16. The system of claim 8 wherein the rim comprises a coil and a tube defining the lumen.

17. The system of claim 8 wherein the rim comprises an inner perimeter and the edge of the fixation section is secured adjacent the inner perimeter.

18. The system of claim 8 wherein the rim comprises a first side and a second side opposite the first side and the fixation section is secured adjacent one of the sides.

19. The system of claim 18 wherein the fixation section comprises a first side and a second side opposite the first side and further comprising a layer of anti-fibrosis material on one of the sides of the fixation section.

* * * * *